US010655096B2

(12) United States Patent
Vellinger et al.

(10) Patent No.: US 10,655,096 B2
(45) Date of Patent: May 19, 2020

(54) BIOMANUFACTURING SYSTEM, METHOD, AND 3D BIOPRINTING HARDWARE IN A REDUCED GRAVITY ENVIRONMENT

(71) Applicant: Techshot, Inc., Greenville, IN (US)

(72) Inventors: John C. Vellinger, Floyds Knobs, IN (US); Eugene Boland, Louisville, KY (US); Michael A. Kurk, Georgetown, IN (US); Krystal Milliner, Georgetown, IN (US); Nester Samuel Logan, Greenville, IN (US)

(73) Assignee: Techshot, Inc., Greenville, IN (US)

( * ) Notice: Subject to any disclaimer, the term of this patent is extended or adjusted under 35 U.S.C. 154(b) by 0 days.

(21) Appl. No.: 15/225,547

(22) Filed: Aug. 1, 2016

(65) Prior Publication Data

US 2017/0029765 A1     Feb. 2, 2017

Related U.S. Application Data

(60) Provisional application No. 62/199,793, filed on Jul. 31, 2015.

(51) Int. Cl.
| | |
|---|---|
| *A61L 27/36* | (2006.01) |
| *A61L 27/38* | (2006.01) |
| *B33Y 10/00* | (2015.01) |
| *C12N 5/00* | (2006.01) |
| *C12M 3/00* | (2006.01) |
| *B33Y 80/00* | (2015.01) |
| *B33Y 30/00* | (2015.01) |
| *A61L 27/54* | (2006.01) |
| *C12M 1/26* | (2006.01) |
| *C12M 1/34* | (2006.01) |
| *B29C 64/106* | (2017.01) |
| *B29C 64/364* | (2017.01) |
| *B29C 64/393* | (2017.01) |
| *B64G 4/00* | (2006.01) |
| *B64G 1/22* | (2006.01) |
| *A01H 4/00* | (2006.01) |
| *B29C 64/40* | (2017.01) |
| *B29K 101/12* | (2006.01) |

(52) U.S. Cl.
CPC ............ *C12M 21/08* (2013.01); *A01H 4/001* (2013.01); *A61L 27/3691* (2013.01); *A61L 27/3895* (2013.01); *A61L 27/54* (2013.01); *B29C 64/106* (2017.08); *B29C 64/364* (2017.08); *B29C 64/393* (2017.08); *B29C 64/40* (2017.08); *B33Y 10/00* (2014.12); *B33Y 30/00* (2014.12); *B33Y 80/00* (2014.12); *B64G 1/22* (2013.01); *B64G 4/00* (2013.01); *C12M 33/00* (2013.01); *C12M 41/40* (2013.01); *C12N 5/0062* (2013.01); *A61L 2300/64* (2013.01); *A61L 2430/20* (2013.01); *B22F 2202/09* (2013.01); *B29K 2101/12* (2013.01); *C12N 2525/00* (2013.01)

(58) Field of Classification Search
CPC ...... C12M 21/08; C12N 5/0062; A01H 4/001;
B33Y 10/00; B33Y 30/00; A61L 27/3895;
A61L 27/3691
See application file for complete search history.

(56) References Cited

U.S. PATENT DOCUMENTS

| | | | |
|---|---|---|---|
| 7,198,940 B2 | 4/2007 | Vellinger et al. | |
| 9,656,426 B2 | 5/2017 | Snyder et al. | |
| 9,764,515 B2 | 9/2017 | Yost et al. | |
| 9,802,355 B2 | 10/2017 | Snyder | |
| 10,052,820 B2 | 8/2018 | Kemmer et al. | |
| 10,086,568 B2 | 10/2018 | Snyder et al. | |
| 2009/0263849 A1* | 10/2009 | Sun | B01L 3/502707 435/29 |
| 2010/0055299 A1 | 3/2010 | Church et al. | |
| 2011/0237002 A1 | 9/2011 | Church et al. | |
| 2013/0017564 A1* | 1/2013 | Guillemot | B01L 3/0268 435/8 |
| 2014/0012407 A1* | 1/2014 | Murphy | B41J 3/407 700/119 |
| 2015/0037445 A1 | 2/2015 | Murphy et al. | |
| 2015/0108687 A1* | 4/2015 | Snyder | B29C 64/106 264/308 |
| 2015/0112472 A1 | 4/2015 | Chen et al. | |
| 2015/0144284 A1 | 5/2015 | Snyder et al. | |
| 2015/0210408 A1 | 7/2015 | Dunn et al. | |
| 2015/0375453 A1 | 12/2015 | Yost et al. | |
| 2016/0082652 A1 | 3/2016 | Snyder et al. | |

(Continued)

FOREIGN PATENT DOCUMENTS

| | | |
|---|---|---|
| CA | 2924078 A1 | 4/2015 |
| CA | 2962090 A1 | 3/2016 |
| CA | 2994277 A1 | 4/2017 |
| CN | 107921564 A | 4/2018 |
| EP | 3027389 A1 | 6/2016 |
| EP | 3147106 A1 | 3/2017 |
| EP | 3238916 A1 | 11/2017 |
| WO | 2012022351 A1 | 2/2012 |

(Continued)

OTHER PUBLICATIONS

Wong, JY et al. 3D printing of surgical instruments for long-duration space missions. Aviation, Space, and Environmental Medicine. Jul. 2014. 85(7): 758-763. Publication date: Jul. 1, 2014. (Year: 2014).*

(Continued)

*Primary Examiner* — Allison M Fox
(74) *Attorney, Agent, or Firm* — Middleton Reutlinger

(57) ABSTRACT

A method, apparatus, and system are provided for the printing and maturation of living tissue in an Earth-referenced reduced gravity environment such as that found on a spacecraft or on other celestial bodies. The printing may be three-dimensional structures. The printed structures may be manufactured from low viscosity biomaterials.

22 Claims, 9 Drawing Sheets

(56) References Cited

U.S. PATENT DOCUMENTS

| | | | |
|---|---|---|---|
| 2016/0101463 | A1 | 4/2016 | Snyder et al. |
| 2016/0221265 | A1 | 8/2016 | Snyder et al. |
| 2016/0243759 | A1 | 8/2016 | Snyder et al. |
| 2016/0282338 | A1 | 9/2016 | Miklas et al. |
| 2016/0288414 | A1 | 10/2016 | Ozbolat et al. |
| 2017/0036783 | A1 | 2/2017 | Snyder |

FOREIGN PATENT DOCUMENTS

| | | | |
|---|---|---|---|
| WO | 2016044837 | A1 | 3/2016 |
| WO | 2017069832 | A2 | 4/2017 |

OTHER PUBLICATIONS

Serway, RA and JS Faughn. College Physics, 4th edition (New York, Saunders College Publishing, 1995), pp. 44, 45, and back cover. (Year: 1995).*

'Facility' definition. The Oxford English Dictionary. [online]. Third Edition, Sep. 2009. [retrieved on Feb. 27, 2019]. Retrieved from the Internet:< URL: http://www.oed.com/view/Entry/67465?redirectedFrom=facility&print>. (Year: 2009).*

European Patent Office, International Search Report and Written Opinion of PCT/US16/45040, 13 pages dated Nov. 8, 2016.

Fabrizio Bensch, Reuters: "World's first 3D-bioprinted transplant-ready organ to be unveiled in early 2015", Nov. 4, 2014 (Nov. 4, 2014), XP002763243 Retrieved from the Internet: URL:https://ww.rt.com/news/202175-3d-bioprinted-organ-transplatn/ [retrieved on Oct. 20, 2016] Nov. 4, 2014.

M. Moody: "3D Bioprinted Thyroid Gland by 2015, Kidney by 2018, Says Russian Scientists", Nov. 9, 2014 (Nov. 9, 2014), XP002763244, Retrieved from the Internet: URL:https://3dprint.com/23805/bioprinted-throid-kidney/ [retrieved on Oct. 20, 2016] Nov. 9, 2014.

Sandford Gary L et al: "Three-dimensional growth of endothelial cells in the microgravity-based rotating wall vessel bioreactor", In Vitro Cellular & Development Biolagy, Animal, Springer US, New York, vol. 38, No. 9, Oct. 1, 2001 (Oct. 1, 2001), pp. 493-504, XP009144922, ISSN: 1071-2690 Oct. 1, 2001.

Rodrigo A Rezende et al: "Development of a Bioreactor by Computer Fluid Dynamics Simulations for the Maturation of 3D Printed Organs by Rapid Prototyping", Chemical Engineering Transactions, Jan. 1, 2013 (Jan. 1, 2013), pp. 1153-1158, XP055312926, Retrieved from the Internet: URL:http://www.aidic.it/cet/13/32/193.pdf [retrieved on Oct. 21, 2016] Jan. 1, 2013.

Sean V Murphy et al: "3D bioprinting of tissues and organs", Nature Biotechnology, vol. 32, No. 8, Aug. 5, 2014 (Aug. 5, 2014), pp. 773-785, XP055244641, US ISSN: 1087-0156, DOI: 10.1038/nbt.2958 Aug. 5, 2014.

* cited by examiner

19

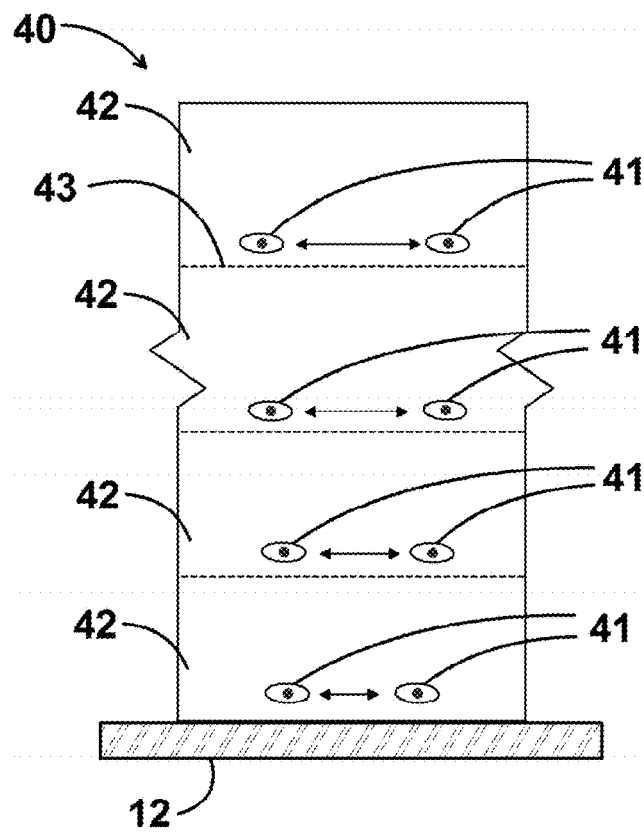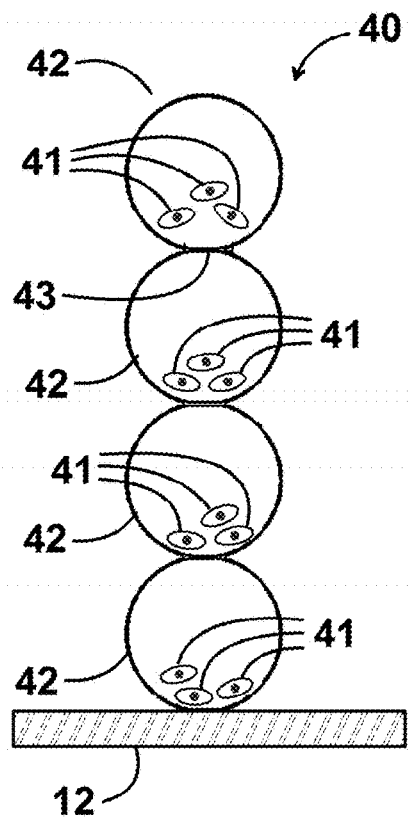
FIG. 8A
PRIOR ART
FIG. 8B
PRIOR ART

BIOMANUFACTURING SYSTEM, METHOD, AND 3D BIOPRINTING HARDWARE IN A REDUCED GRAVITY ENVIRONMENT

BACKGROUND

The present embodiments relate to a system, method, and apparatus for bioprinting in a reduced gravity environment.

SUMMARY

In some embodiments, a method for the additive manufacturing of living tissue in a reduced gravity environment may comprise one or more of the steps of providing a reduced gravity environment, providing a housing having a bioprinter, providing one or more bioinks, and printing one or more three-dimensional tissues with the one or more bioinks from said bioprinter within the reduced gravity environment. One or more three-dimensional tissues may be printed in a bioreactor. In use, the bioreactor may be positioned on at least one print stage of the bioprinter. Another step may include positioning the one or more three-dimensional tissues into a bioreactor after printing. The one or more three-dimensional tissues may be positioned into the bioreactor manually or automatically. Further one or more bioinks may include non-living biological components such as at least one of natural or synthetic structural proteins, polymers, macromolecules, or pharmaceuticals. The reduced gravity environment may be an environment wherein the gravitational acceleration is less than 9.807 meters per second per second. In addition, one or more bioinks may include living biological components such as at least one of undifferentiated stem cells, partially differentiated stem cells, terminally differentiated cells, microvascular fragments, or organelles.

In addition, in some embodiments, the method may include the step of maturing one or more three-dimensional tissues. The one or more bioinks may have a viscosity range of approximately 1 to 10,000,000 centipoise, preferably the viscosity range is approximately 5 to 2,000 centipoise. Another step may include controlling at least one of temperature or humidity. Further steps may include providing one or more print stages and controlling the thermal characteristics of the one or more print stages.

In some embodiments, further steps may provide one or more print heads and controlling the thermal characteristics of the one or more print heads. There may be additional steps of controlling the temperature of one or more bioinks. Additional steps of at least partially controlling the additive manufacturing of living tissue in the reduced gravity environment from one or more locations may be used. The one location may be terrestrial. The one or more three-dimensional tissues may be transported from the reduced gravity environment to a different gravity environment. The different gravity environment may be at least one of a terrestrial environment or an extraterrestrial environment. Another embodiment may include the step of incorporating prefabricated structure into one or more three dimensional tissues for at least one of the creation of the tissue or organ, support structure, perfusion aid, implantation aid, cell delivery, or reagent delivery.

In some embodiments, a biomanufacturing system capable of assembling and maturing living tissue in a reduced gravity environment from one or more bioinks may include a bioprinter, a cell culturing device, one or more bioinks, and an environment of reduced gravity surrounding the bioprinter and the cell culturing device. The bioprinter may be a three dimensional printer. Further the bioprinter may be separate from the cell culturing device. The cell culturing device may include at least one of a mechanical tissue stimulation or electrical tissue stimulation.

In addition, in some embodiments, one or more print heads of the bioprinter may be in fluid communication with the interior of the cell culturing device. Further the environment of reduced gravity may be temperature controlled and/or humidity controlled. In addition, one or more bioinks may have a viscosity range of approximately 1 to 10,000,000 centipoise, preferably the viscosity range is approximately 5 to 2,000 centipoise. The environment of reduced gravity may have a gravitational acceleration less than 9.807 meters per second per second. Further in some embodiments, at least one of the cell culturing device or the one or more bioinks downstream of the bioprinter may be transported from the environment of reduced gravity to an environment having a different gravity. In some embodiments, the system is a modular configuration. The modular configuration may include both major systems and some individual components that may be swapped-out for resupply, refurbishment, or upgrade. The modular configuration may include one or more of captive fasteners, self-aligning blind-mate electrical and mechanical connectors, grouping of low mean time between failure (MTBF) and high MTBF components, grouping of certain electrical components within electromagnetic interference shielding, and/or colocation of elements requiring air or liquid cooling. In addition, the cell culturing device may include an integrated life support system for transportation of living tissue from said environment of reduced gravity to an environment having a different gravity.

Further, in some embodiments, an additive manufacturing apparatus may include a reduced gravity environment, a bioprinter positioned in the reduced gravity environment such that the bioprinter has one or more print heads in relation to at least one print stage, and one or more bioinks have a viscosity range of approximately 1 to 10,000,000 centipoise in fluid communication with the one or more print heads. The bioprinter may be a three-dimensional printer.

In addition, in some embodiments, the apparatus may have a bioink dispensing system, a visualization system capable of observing a top surface of the print stage, an x-axis translation system, a y-axis translation system, and a z-axis translation system, and wherein at least one of the one or more print heads allow direct write constant pressure extrusion. Further embodiments may include one or more bioreactors. The viscosity range may be approximately 5 to 2,000 centipoise. In addition, one or more thermoplastics may be in fluid communication with the one or more print heads. Further the housing may have at least one of temperature control or humidity control. In some embodiments the apparatus is a modular configuration. The modular configuration may include both major systems and some individual components that may be swapped-out for resupply, refurbishment, or upgrade. The modular configuration may include one or more of captive fasteners, self-aligning blind-mate electrical and mechanical connectors, grouping of low mean time between failure (MTBF) and high MTBF components, grouping of certain electrical components within electromagnetic interference shielding, and/or colocation of elements requiring air or liquid cooling.

These and other advantages and features, which characterize the embodiments, are set forth in the claims annexed hereto and form a further part hereof. However, for a better understanding of the embodiments, and of the advantages and objectives attained through its use, reference should be made to the Drawings, and to the accompanying descriptive matter, in which there is described example embodiments. This summary is merely provided to introduce a selection of concepts that are further described below in the detailed description, and is not intended to identify key or essential features of the claimed subject matter, nor is it intended to be used as an aid in limiting the scope of the claimed subject matter.

BRIEF DESCRIPTION OF THE FIGURES

In the drawings, like reference characters generally referred to the same parts throughout the different views. Also, the drawings are not necessarily to scale, emphasis instead generally being placed upon illustrating the principles of the invention.

FIG. 8A is an enlarged side view of a portion of a prior art additive structure influenced by the negative effects of gravity.

FIG. 8B is a sectional view of the prior art additive structure of FIG. 8A influenced by the negative effects of gravity.

DETAILED DESCRIPTION

Figure 1:
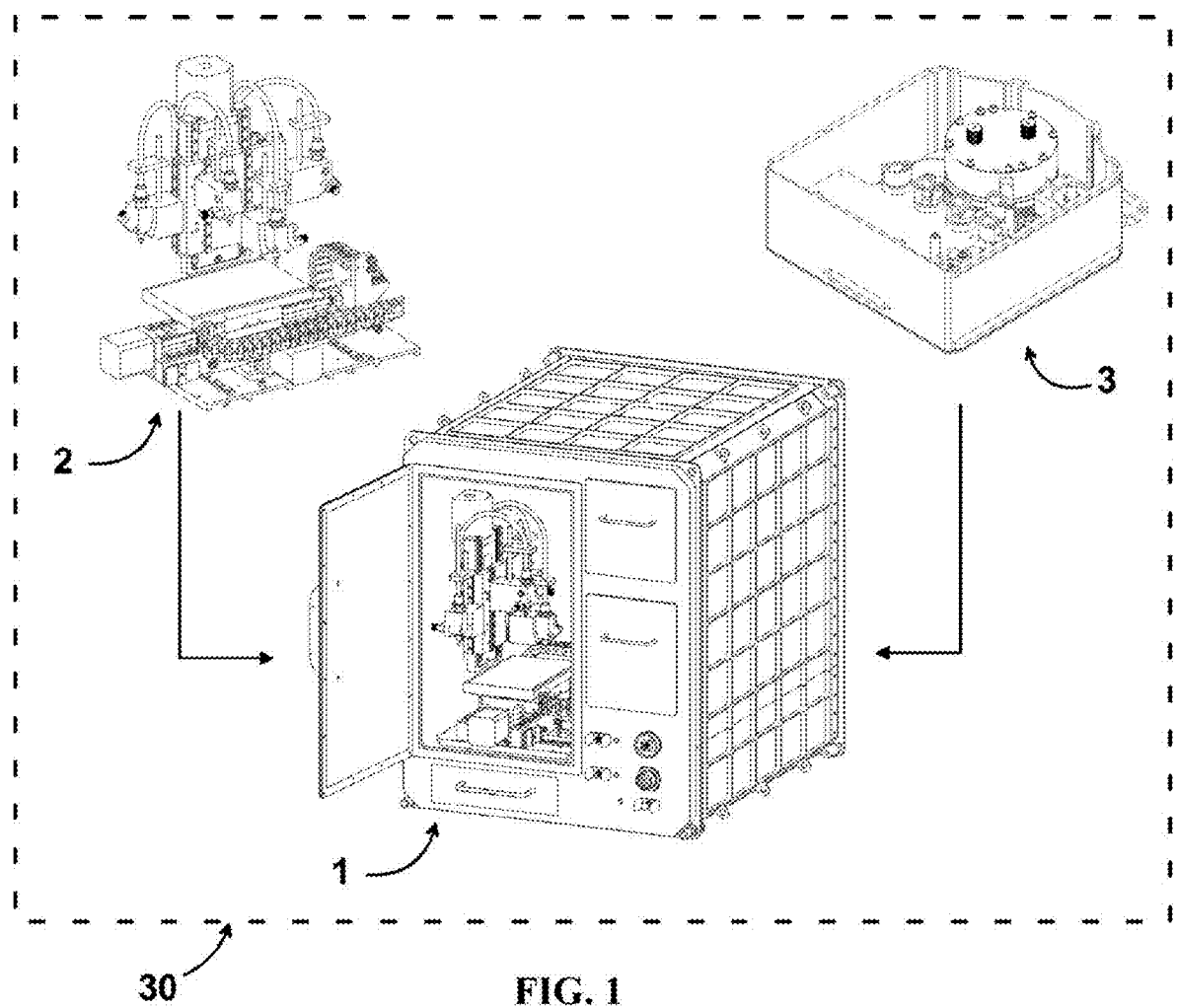
FIG. 1 illustrates an embodiment of the biomanufacturing system wherein the cell culturing bioreactor and 3D bioprinter are combined in a single integrated biomanufacturing facility capable of manufacturing tissue in reduced gravity, showing the bioprinter and the bioreactor outside the enclosure for clarity.
Figure 2:
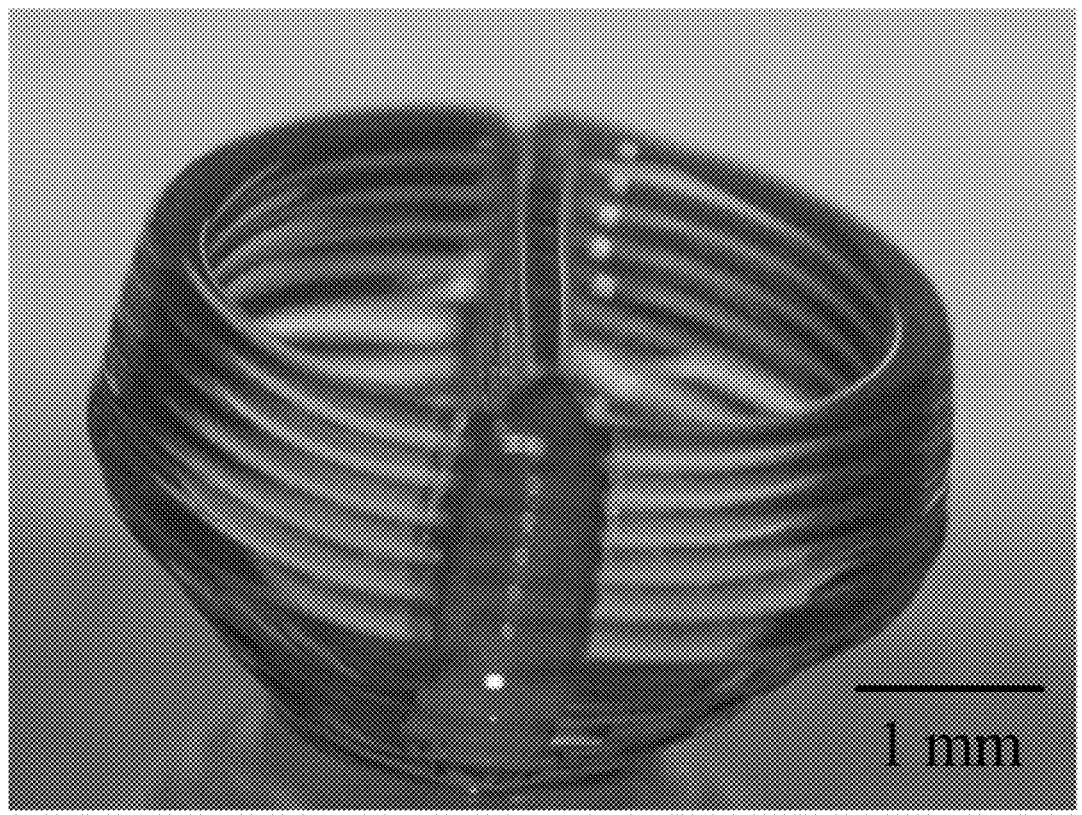
FIG. 2 is a perspective view of a prior art heart ventricle influenced by the negative effects of gravity; the material of the 3D printed structure flowed out of the desired geometry due to gravity.

Various embodiments of the invention may include a biomanufacturing system, method, and 3D bioprinting hardware optimized for exclusive use in a reduced gravity environment 30 such as that found on an orbiting spacecraft (microgravity) or another celestial body (fractional gravity). FIG. 1 illustrates a cell culturing device or bioreactor 3, a 3D bioprinter 2, and/or integrated biomanufacturing facility 1 capable of manufacturing tissue in reduced gravity. In the partial or complete absence of gravity, this system is able to construct tissues using bioinks with lower viscosities than are currently feasible for all Earth-based bioprinters. Lower viscosities allow faster printing without damaging the cells, proteins, and biomacromolecules from the effects of cavitation, high pressure, or chemical crosslinking agents. Another advantage of lower viscosity is cell motility within the printed tissue. This allows the tissues to mature faster and reduce hindrance in the formation of vascular beds used for thick tissue viability. FIG. 2 illustrates a prior art heart ventricle 4 influenced by the negative effects of gravity, resulting in deformity out of the desired shape. This deformity out of the desired pattern may result in improper function.

In addition to reduced viscosity, tissues can be built in the biomanufacturing facility 1 without or with reduced external support structures. In traditional, terrestrial additive manufacturing, overhangs may be supported either with the same material or a separate material. In either case, this material is removed after processing as it is not part of the desired tissue or end product; it is merely a means to perform bottom-up construction. In the absence of a pronounced gravitational vector, such as in the environment in Low Earth Orbit (LEO), these tissues can be built with only the functional components. This reduces the risk that supports may be forgotten and left in a tissue, or left out and have an inner passage form incompletely. Additionally, more complex geometries can be produced containing enclosed void volumes, such as the four chambers of a heart, that are unattainable using similar systems on Earth.

Finally, basic stem cell research on the International Space Station (ISS) has demonstrated improved proliferation, maturation, and differentiation. Expanding upon these findings during the culture phase of this system can produce more robust tissues and produce those tissues faster and more easily. This allows the system to use lower cell concentrations and culture for shorter periods of time than Earth-based systems to produce the same or superior tissue. For complex tissues, this time savings could be substantial. Therefore, overall both the quality and quantity of the bio tissue may be dramatically improved in reduced gravity.

The reduced gravity biomanufacturing facility 1 comprising a 3D bioprinter 2 and a cell culturing bioreactor 3, is designed to manufacture 3D living tissue in a reduced gravity environment 30 such as the microgravity environment of an orbiting spacecraft or the fractional gravity environment on the surface of other celestial bodies such as Earth's moon (1.622 meters/second/second or about one-sixth Earth's gravity) or Mars (3.711 meters/second/second or about one-third Earth's gravity). For reference, the surface of planet Earth is considered to have a unit gravity, or "1-g" environment equivalent to 9.807 meters/second/second. Microgravity is a term often used to describe the weightless conditions experienced aboard a vehicle in a state of continuous free fall as, for example, on a spacecraft in orbit around a planet. A reduced gravity environment, therefore, is any environment with a gravitational acceleration less than that of the Earth environment. The physical effects of a reduced gravity environment are a key component of successful biomanufacturing. Since the biomanufacturing equipment uses a human habitable environment (atmosphere, thermal) for living tissue, a variety of applications of, but is not limited to, microgravity spaceflight platforms may include International Space Station, commercial space stations such as the Bigelow Aerospace B330, or free-flyers such as the Space Exploration Technologies Corporation (SpaceX) DragonLab, Boeing CST-100 Starliner, or Sierra Nevada Corporation Dream Chaser®. Fractional gravity platforms might include rotating spacecraft or habitable facilities on or beneath the surface of the moon, Mars, an asteroid, or other extraterrestrial celestial bodies.

Figures 9A, 9B:
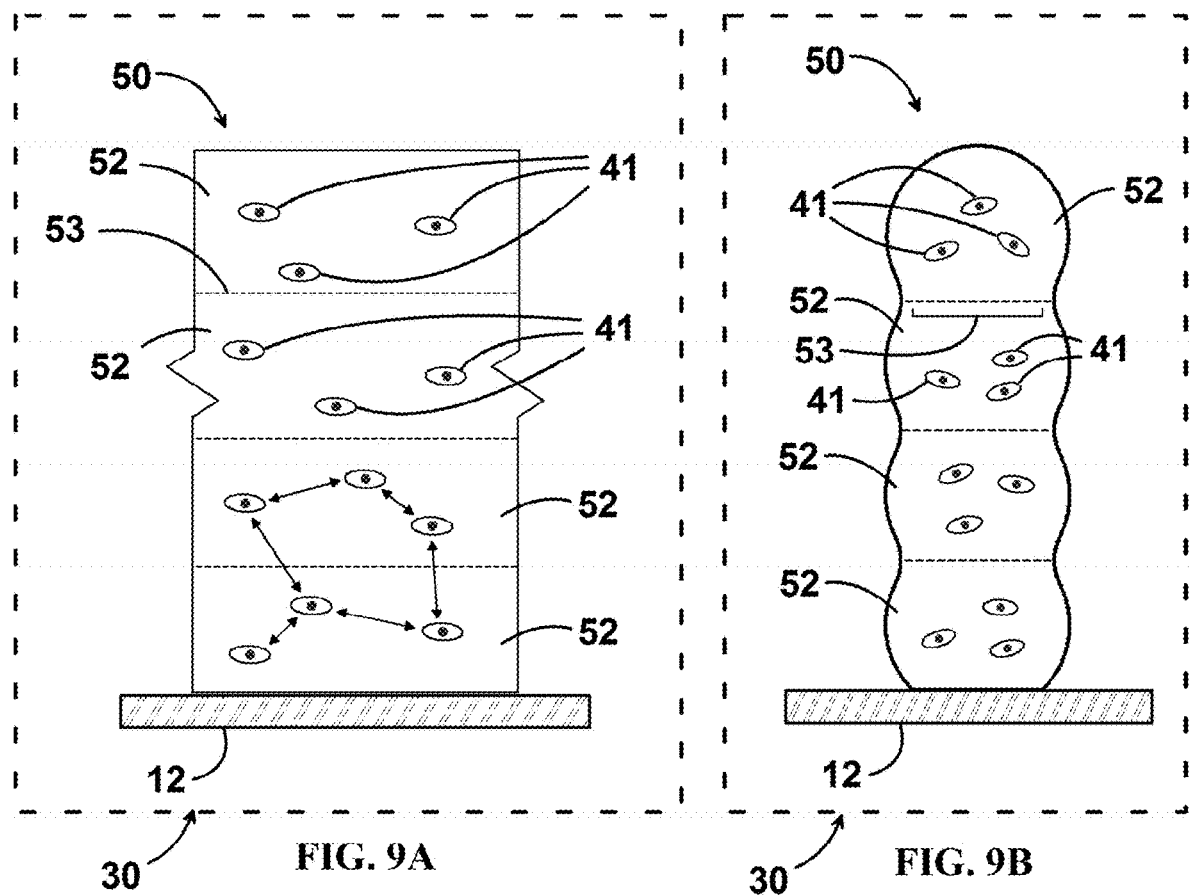
FIG. 9A is an enlarged side view of a portion of an embodiment of the additive structure printed in a reduced gravity environment.
FIG. 9B is a sectional view of the embodiment of the additive structure of FIG. 9A.

With reference to the prior art 4-layered printed wall 40 of FIGS. 8A and 8B representing printing on Earth and a similarly constructed 4-layered printed wall 50 of FIGS. 9A and 9B representing printing in reduced gravity, several advantages to reducing or removing gravity from the process are evident. Sedimentation within fluids does not occur. Under the influence of gravity, cells 41 sediment down to the 'bottom' of each printed bead 42. Even after subsequent proliferation, this initially heterogeneous distribution of cells can result in structurally weaker, less densely populated 'top' portions of each printed bead 42. Buoyance-driven stratification can also occur within the bulk material of each bead 42. Conversely, the cells 41 and bulk material of printed wall 50 are naturally homogeneous in their positions throughout. Lower viscosity fluids can be formed into 3D printed structures that still maintain their desired shapes without the complication of gravity-induced deformation. The use of lower viscosities allows faster printing without damaging the cells, proteins, and biomacromolecules from the effects of cavitation, high pressure, or chemical cross-linking agents.

Another advantage of lower viscosity is cell motility within the printed tissue and cell interaction both within a bead of printed material and across the boundary between beads of printed material. This allows the tissues to mature faster and reduces hindrance to the formation of vascular beds used for thick tissue viability. Again with reference to FIGS. 8A, 8B, 9A, and 9B, prior art FIGS. 8A and 8B show the geometry resulting from the use of high viscosity fluids to create prior art printed wall 40. Individual beads 42 virtually retain their circular cross section resulting in steep contact angles between successive beads 42 and a relatively small contact interface 43. High viscosity fluids will adhere to one another, but do not readily meld or intermix, so the area of the contact interface 43 can act as a physical barrier to both mass transport and cellular interaction between adjacent beads 42. Delamination between successive beads 42 can also occur due to the relatively small contact interface 43 and hindered ability for cells to interconnect across this interface. Conversely, and advantageously, the low viscosity beads 52 of printed structure 50 readily meld, the contact angles between adjacent beads 52 approach zero degrees as the material 'self levels' along its height due to surface tension, and contact areas 53 between adjacent beads 52 all but disappear. The resulting printed structure 50 has a much more uniform overall width, cell and extracellular material distribution, and integrity.

In a reduced gravity environment, 3D bioprinter 2 can print using low viscosity extrudable materials, hereafter referred to as bioinks, that may have one or more of the following components: natural and synthetic structural proteins, such as fibrinogen, albumin, fibronectin, collagen, or hyaluronic acid; polymers, such as pluronic or urethanes; living biological components, such as undifferentiated stem cells, partially differentiated stem cells, terminally differentiated cells, microvascular fragments, or organelles; macromolecules; or pharmaceuticals. These bioinks may have a viscosity as low as approximately 1 centipoise on the low side, and have viscosities on the high side of typical bioinks used in terrestrial applications (for example, on the order of 10,000,000 centipoise). Preferably the range of viscosity is approximately 5 to 2,000 centipoise. On Earth, under the influence of gravity, structures printed using such low viscosity bioinks cannot maintain their initial shape and will deform or structurally fail under their own weight. Internal and/or external scaffolds of like or dissimilar materials may be constructed to maintain the initial shape. These scaffolds are subsequently removed. However, in a reduced gravity or near-weightless environment, complex shapes such as cantilevered overhangs and enclosed voids, such as the enclosed chambers of a heart, can be easily maintained. Yet another advantage of printing in a reduced gravity environment is the ability to build up cantilevered overhangs that simply cannot be made on Earth, even with supporting scaffolds. On Earth, each new extruded bead typically contacts 75% or more along the length of the bead directly beneath it. Therefore it utilizes many stacked but only slightly offset layers to incrementally build a cantilevered structure. In a reduced gravity environment, the goal is to create structures wherein less than 50% of a new extruded bead makes contact along the length of the bead directly beneath it. This will enable thinner overall printed structures and steeply cantilevered geometries that simply cannot be made on Earth using any conventional means.

FIG. 2 demonstrates the root cause of further benefits of printing in reduced gravity using low-viscosity bioinks. In the additive manufacturing process of bioprinting, material is extruded in successive layers. The high viscosity bioinks used to terrestrially print the ventricle 4 shown in FIG. 2 maintain clearly distinct layers on the final structure. The boundaries between successive layers act as both physical and chemical barriers to cell proliferation. Cells can relatively easily interact within a single layer, but not across layer boundaries. The use of low viscosity bioinks advantageously results in little or no clearly defined layers in the resulting 3D printed structure, thereby promoting and accelerating the interaction between cells in different layers and leading to a more robust final product.

Figure 3:
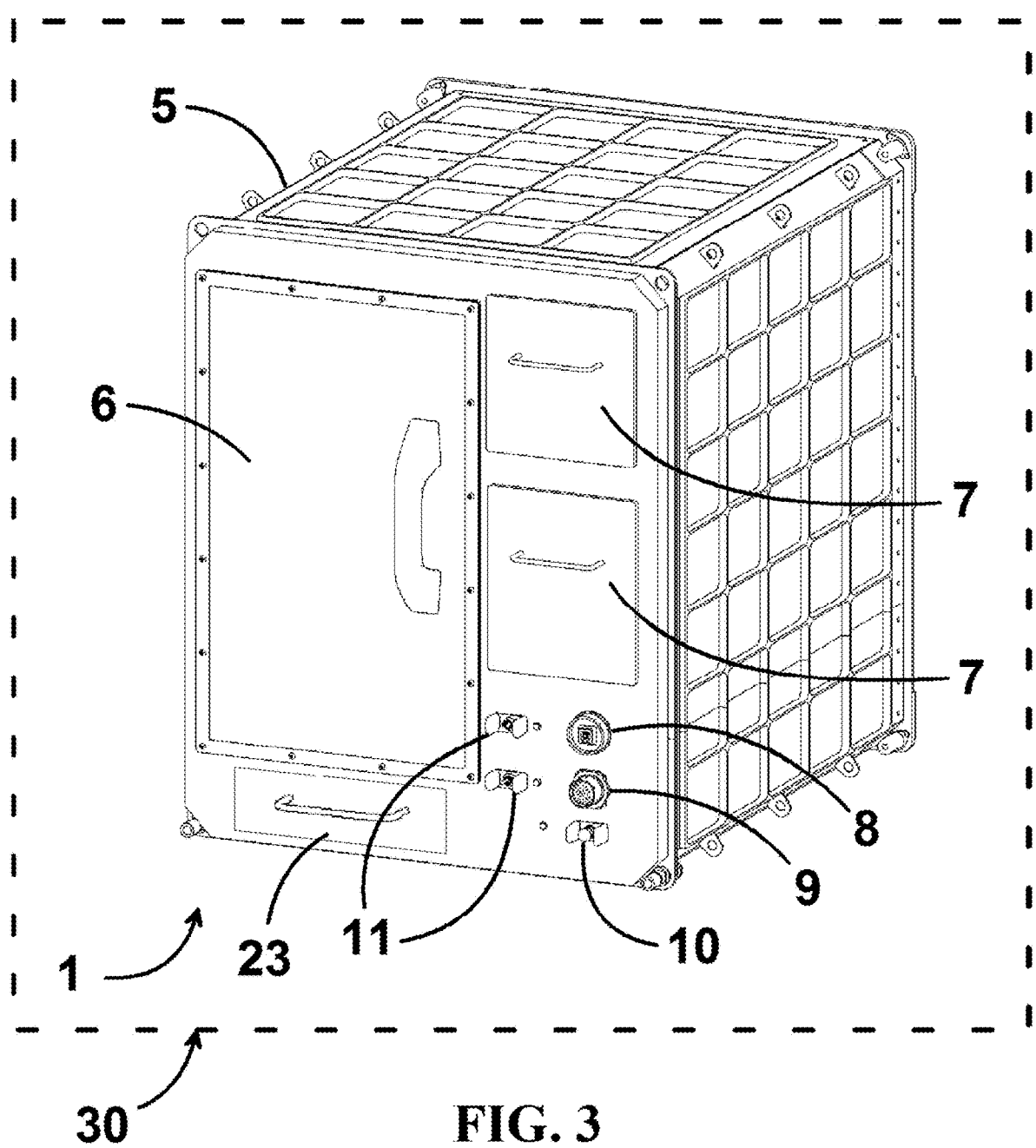
FIG. 3 is a perspective view of the integrated reduced gravity biomanufacturing facility of FIG. 1 with the door closed.
Figure 4:
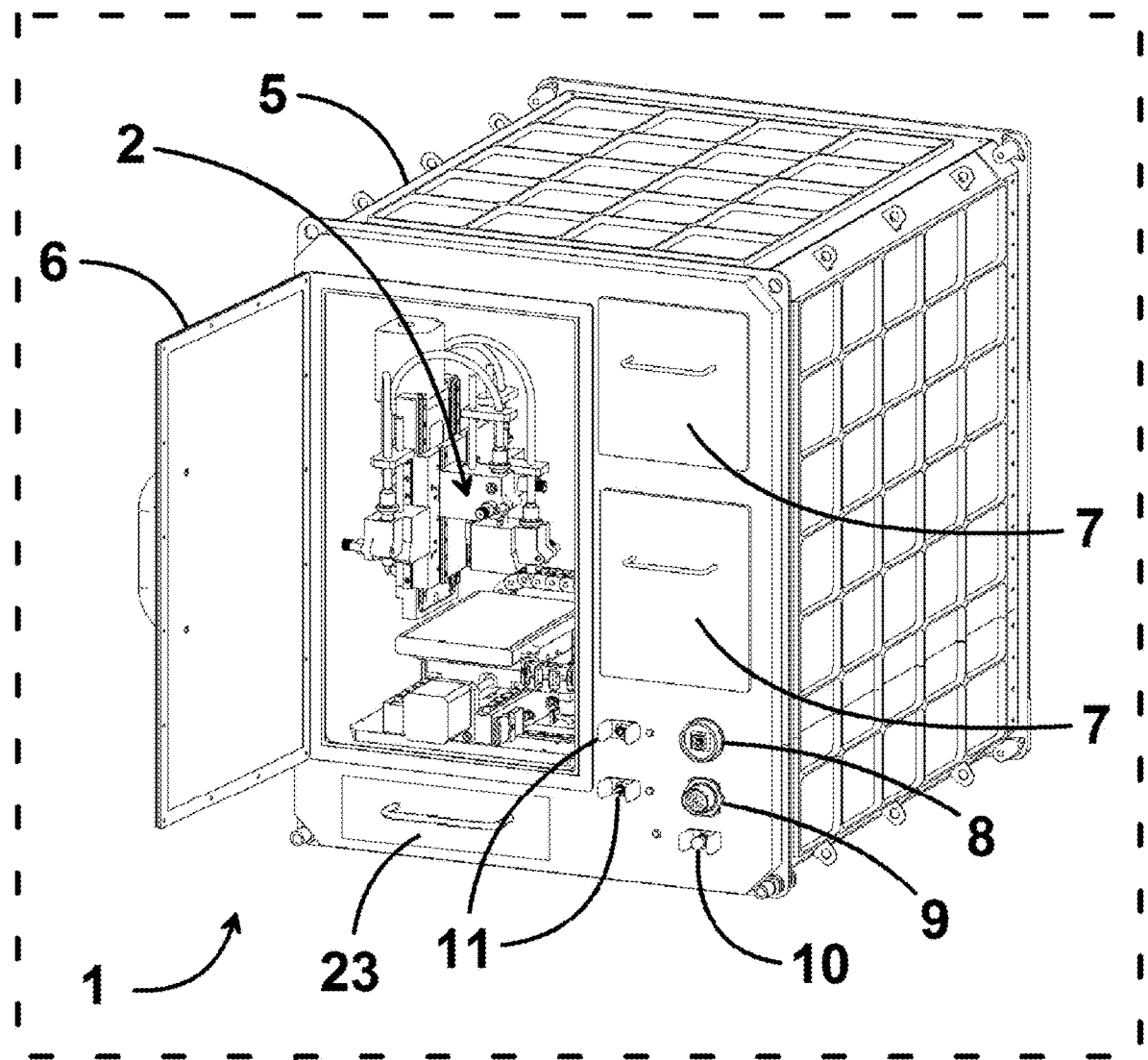
FIG. 4 is a perspective view depicting the general layout of some of the exterior biomanufacturing facility components with the door open.

The reduced gravity biomanufacturing system comprises, at a minimum, two major subsystems: a 3D bioprinter and a cell culturing bioreactor in which a printed structure is incubated to promote cell proliferation, differentiation, and remodeling into a final product tissue. In one embodiment, both subsystems occupy discrete and separate facilities. Precautions may be taken to prevent physical damage or exposure to deleterious environmental microorganisms during transfer between subsystems. In a preferred embodiment, both subsystems are contained within a single integrated facility. This embodiment reduces or eliminates moving a structure from bioprinter to bioreactor and protects the biomaterial during all stages of processing. FIGS. 3 and 4 show an embodiment of the reduced gravity biomanufacturing system whereby both 3D bioprinter 2 and bioreactor 3 are housed in one integrated biomanufacturing facility 1. Biomanufacturing facility 1 is a modular box-like volume with an overall geometry compatible with the generic interface requirements for various spacecraft or habitable systems. External enclosure or housing 5 includes a door 6 for operator access to the environmentally controlled interior chamber where 3D bioprinter 2 and cell culturing bioreactor 3 (not shown) reside. External enclosure 5 surrounds and supports the individual assemblies and components within the unit and has exterior dimensions, in the embodiments shown, that are approximately 21 inches×21 inches×18 inches (essentially a spaceflight double locker typical of the art). Several notional switches 11 enable overall power to major subsystems. Circuit breaker 10 provides facility over-current protection consistent with the requirements levied by the habitable platform. Power connector 9 and data connector 8 are typical multi-pin shrouded connectors typical in the art for providing electrical interfaces to a vehicle or facility. Consumables bays 7 house stock materials that are consumed by the 3D bioprinter 2 or cell culturing bioreactor 3 major subsystems. Consumables may include one or more of bioinks used to print 3D structures, media to perfuse a 3D printed structure during cell proliferation, thermoplastic feed stock that can be used to manufacture in situ bioreactor enclosures, and compressed gas supplies such as oxygen used to maintain culturing cells. The hardware is designed in a modular configuration so that both major systems and some individual components can easily be swapped-out on orbit for resupply, refurbishment, or upgrade as technology advances. Modularity is further facilitated by design features such as the use of captive fasteners that cannot be lost during removal in reduced gravity; self-aligning blind-mate electrical and mechanical connectors between modular subsystems; logical grouping of low mean time between failure (MTBF) and high MTBF components separately to minimize the mass and volume of replacements; grouping of certain electrical components within electromagnetic interference shielding; and colocation of elements requiring air or liquid cooling such as power supplies, thermoelectric Peltier devices.

A computerized command and data management system (CDMS)/power supply 23 provides power, monitors, and controls operation of the facility 1. The electrical system components and topology are typical of those in the art of manufacturing high reliability, high safety equipment for the medical, defense, or aerospace fields. For example, the present invention uses a federated control architecture to reduce the risk of major system failure resulting from the radiation and high-energy particles often encountered in reduced gravity environments such as space. (CDMS)/power supply 23 conditions the power and provides the voltage levels used by the biomanufacturing facility as well as providing electromagnetic interference filtering and electrical bonding. Software employed internally to operate and control components such as pumps, sensors, motors, and data acquisition are typical for computer controlled electromechanical systems. Facility 1 has the ability to monitor and control all of the system parameters real time with the added flexibility of being able to uplink and downlink files, video, and operating data at any time. The facility uses software and physical interfaces to various host vehicles or platforms that are compatible with command and control interfaces typical in the art such as universal serial bus (USB) and Ethernet. It may incorporate a digital display with a user-friendly graphical user interface (GUI). CDMS/power supply 23 may be housed within enclosure 5 or may be a separate entity (not shown) connected via cables (not shown) to respective data connector 8 and power connector 9. In a general sense, tasks performed by the biomanufacturing system may be performed manually by an operator, semi-autonomously, or fully autonomously with or without remote monitoring. For example, the remote monitoring may be at least partially from a terrestrial location. Biomanufacturing facility 1 may be ergonomically designed to facilitate ease of use by an operator in a reduced gravity environment.

Figure 5:
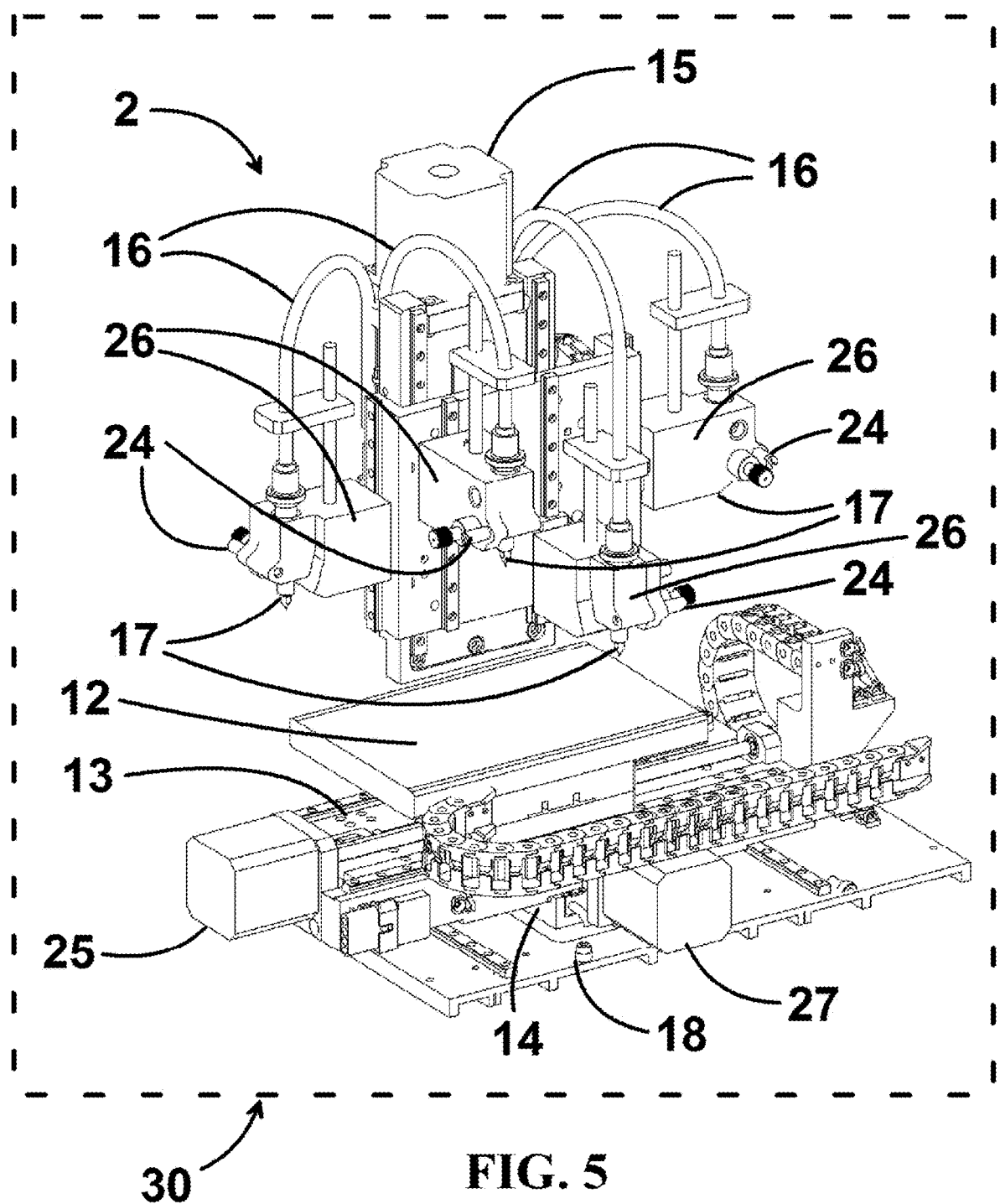
FIG. 5 is a perspective view of the reduced gravity 3D bioprinter print stage and interdependent systems that translate the stage and feed the bioinks to the print heads.

FIG. 5 describes the reduced gravity 3D bioprinter 2 in greater detail. One or more print stages 12 comprises a flat plate that can be thermally controlled as desired. This plate may be metallic or nonmetallic, surface treated or untreated, removable or non-removable. In a preferred embodiment, print stage 12 is mounted to x-axis support structure 13 and y-axis support structure 14. Print stage 12 translates in two axes utilizing X-motion control system 25 and Y-motion control system 27 to move in the X-direction and Y-direction respectively. In the preferred embodiment, control systems 25 and 27 comprise computer controlled brushless DC servo motors common in the art to control the accuracy, repeatability, resolution, and velocity of print stage 12 during the bioprinting process. Support structures 13 and 14 are mounted within enclosure 5 via vibration isolators 18 to further facilitate precision in the printing process. Z-axis support structure 15 is mounted on an interior sidewall of enclosure 5 directly above print stage 12. Each print head 17 includes an associated visualization system 24 and dispensing system 16 that will be described hereafter in greater detail. In a preferred embodiment, one or more print heads 17 each include individual Z-motion control systems 26 capable of independently translating print heads 17 in a third, or Z-, axis that is substantially orthogonal to the x-y plane defined by print stage 12. For example, control system 26 may comprise one or more computer controlled brushless DC servo motors to control the accuracy, repeatability, resolution, and velocity of one or more print heads 17 during the bioprinting process. In an enhanced embodiment, additional means for Z-axis translation of dispensing system 16, and all print heads 17 may be desirable to facilitate post-printing access to print stage 12. Using one or more translation or motion control systems such as but not limited to 25, 26, and 27, the relative position of print stage 12 and interdependent systems can translate in the x-, y-, and z-directions up to about 12 inches and feed stock to the print heads in the embodiment shown. In a second embodiment, print stage 12 and, optionally, visualization system 24, may translate in the z-direction while print heads 17 and dispensing system 16 may translate in the x- and y-directions. In a third alternate embodiment, print stage 12 may remain in a fixed location while z-axis support structure 15 and dependent elements may translate in the x-, y-, and z-directions. In a fourth alternate embodiment, z-axis support structure 15 and dependent elements remain fixed while print stage 12 may translate in the x-, y-, and z-directions. Each of the three alternate embodiments utilize different associations with motion control systems 25, 26, and 27 than shown in the preferred embodiment of FIG. 5. While weightless, or nearly weightless, the printed structure still experiences momentum. Abrupt changes in direction of the printed structure may result in deformity. In some combinations of translation interdependency described above, the printed structure remains stationary or moves minimally in the x-direction, particularly those wherein print heads 17 translate in the x- and y-directions. In combinations wherein print stage 12, and hence the printed structure, translate in the x- and y-directions, both translation acceleration and velocity are carefully controlled to mitigate momentum effects.

Working in concert with print stage 12 is multi-solution dispensing system 16 that incorporates precision control of the feed rates of the bioink fluids delivered to one or more removable and replaceable print heads 17. Being a dynamic system capable of 6-axes of freedom, dispensing system 16 is also able to maintain dynamic flow control during the bioprinting process all within a thermally controlled environment. Dispensing system 16 also provides precise start and endpoint volumetric control. Print technologies comprise two groups: point by point "ink jet" printer-based, also called laserjet printing, or point and line "direct write" syringe-based. In a direct write system, pressure is maintained, either mechanically (linear motor, drive screw) or pneumatically (vacuum, pressurized gas, pressurized drive fluid), on a reservoir of bioink that is ejected through a small gauge needle or extruder tip to the printing substrate which is often temperature controlled. Feed is enabled by control of a valve (not shown). The feed rate and the ability to start and stop the flow of material differentiate the systems as well as the ability to handle a wide range of working fluid viscosities. The preferred embodiment utilizes direct write print heads such as the SmartPump™ manufactured by nScrypt, Inc. (Orlando, Fla.) and may use either a very fine needle or a very fine ceramic tip extruder. The diameter of the extruded material is typically in the range of 12.5 to 125 micrometers. A plurality of print heads can be simultaneously or serially orchestrated to incorporate several different bio-inks into the printed structure. This feature may allow the production of complex structures such as organs that may utilize several different functional tissue types. As described below, some print heads may print non-biological material such as thermoplastics to build in situ bioreactor vessels or electrically conductive material to electrically connect prefabricated sensors that can be incorporated into the 3D printed tissue. Surfaces of print heads 17 and/or print stage 12 may be natively, or treated to be, hydrophobic or hydrophilic in order to urge the proper behavior of the extruded bioinks. Physical forces such as surface tension are known to play a more dominant role in reduced gravity fluid dynamics.

Illuminated visualization system 24 may have one or more small cameras, associated with each print head 17, focused on print stage 12 plus either visible or infrared illumination as is typical in the art such as LED lighting. Visualization system 24 may incorporate the ability to capture both still and video images of the entire bioprinting process. The frame rate, resolution, and field of view are all fully programmable. Illumination can be turned on or off by an operator as desired. Observation of the structure during printing enables an operator, one who may be observing directly or via remote telemetry, to make real time corrections as the print develops.

A quiescent, biologically compatible environment may be provided during one or more steps of the biomanufacturing process. One or more components of the biomanufacturing facility 1 can control both the temperature and humidity environment. Typical spacecraft ambient environments are in the temperature range of 20-25° C. with a low relative humidity in the range of 30-50%. The enclosable internal volume of biomanufacturing facility 1 surrounding 3D bioprinter 2 can be maintained and controlled at approximately the same ambient temperature in the range of 20-25° C., but relative humidity may be controlled at an elevated but noncondensing 70-90% in order to mitigate desiccation of the printed structure while it is being processed. Atmospheric control systems used to heat, cool, humidify, and dehumidify enclosed volumes in a habitable reduced gravity environment are well known in the art of closed environmental life support systems used in spacecraft design. Some components of 3D bioprinter 2, specifically, print stage 12 and print heads 17, may have active thermal control independent of the bulk internal volume environment to enhance the quality and integrity of the biomaterial being printed. If desired to be used, certain chemical or biochemical reactions of the bioinks utilize heating or cooling relative to the ambient environment of the 3D bioprinter at the time of extrusion or incorporation into the printed structure. The bioreactor encloses the 3D printed structure and bathes it in liquid media thermally controlled to maintain the body temperature of the organism compatible with the printed tissue. Typically, this will be human body temperature of approximately 37° C. The facility is designed with vibration isolation for the print stage to insure the material is printed with high precision.

After the tissue is printed, whether in the present bioprinter 2 or another, these neo-tissues need to mature before they gain the strength and function to be transplantable. This maturation will be accomplished in a bioreactor 3 that utilizes a feedback control system to supply the growing tissue with oxygen and nutrient medium (glucose, trace elements, etc.), remove waste metabolic products and carbon dioxide, maintain optimal pH, minimize the accumulation of air bubbles, and facilitate cell proliferation, differentiation, and tissue remodeling. The design of compatible bioreactors is well known in the art including bioreactors designed for use in low gravity (such as in U.S. Pat. No. 7,198,940 incorporated herein by reference). Typically they include means (not shown) for a liquid media supply reservoir, a liquid waste reservoir, pumps for circulating media, heating and cooling, oxygenation, degasification, sensors, and monitored feedback control systems.

In one embodiment, the printed structure may be physically removed from print stage 12 and transferred into a separate cell culturing bioreactor 3 by an operator or robot. In this embodiment, bioreactor 3 may be collocated along with bioprinter 2 within biomanufacturing facility 1. Alternatively, bioreactor 3 may be in a different location not associated with biomanufacturing facility 1. A removable bioreactor 3 may be packaged to include its own integrated life support systems so that it can serve a second function of maintaining the printed and cultured tissue in fluid living homeostasis for transportation and return to a patient on Earth or an alternate, extraterrestrial destination. Such a 'transportation compatible bioreactor' would include adequate robustness of design to survive the vibration environment experienced during planetary descent and possible refrigeration necessary to extend longevity of the printed and cultured tissue. In an alternate embodiment, a removable bioreactor 3 may be designed to interface with a host transportation carrier capable of providing power and life support to at least one bioreactor during transportation and return.

In a second embodiment, the print stage itself may be transformed into a cell culture type vessel that becomes bioreactor 3. This may be accomplished by simultaneously or serially printing both a bioink and a thermoplastic using two print heads to create both the biological structure and its enclosing culture vessel.

In a third embodiment, bioreactor 3 may comprise an open-topped prefabricated and pre-plumbed enclosure 20 mounted on print stage 12. This third embodiment allows print head 17 the requisite access to print stage 12 to dispense the bioinks within pre-plumbed enclosure 20. Once the bioprinted structure is completed, either a prefabricated lid may be installed and sealed on enclosure 20 to create bioreactor 3 or, alternatively, a second print head 17 could extrude thermoplastic to print a lid or top fastener directly on prefabricated enclosure 20.

Any of these embodiments may be enhanced by bioreactor 3 providing any of equibiaxial mechanical loading in tension, electrical stimulation, fluid shear, or compression. Mechanical loading in tension may be provided by printing the tissue construct on a flexible membrane. On the opposite side of the flexible membrane, a pressure or vacuum source may be attached causing the membrane to distend and impart tension into the tissue. This stretching is known to induce maturation in many cell types including cardiomyocytes. The bioreactor may include means to both induce and monitor electrical stimulation for depolarization currents in cardiac tissues. The ability to capture the spontaneous contraction of cardiomyocytes and pace a tissue is another indication of maturation. Terrestrial bioreactors providing mechanical loading, electrical stimulation, fluid shear, or compression are known in the art.

One embodiment of the reduced gravity biomanufacturing system having the previously described hardware can have at least one suite of software tools to create, edit, import, model, simulate, and control the biomanufacturing system to produce the tissue and the supporting structures or components for the creation, culture, transfer, or implantation of the printed tissue. The system can import and modify image files from medical imaging formats to create geometries defining tissues or organs to be printed. The imaging technology can be selected from magnetic resonance imaging, computerized tomography, X-ray radiography, medical ultrasound, endoscopy, tactile imaging, medical photography, positron emission tomography, and nuclear magnetic resonance imaging. The system may output an electronic model file used by another software or hardware platform to visualize the tissue before 3D printing. The biomanufacturing system software tools can modify the tissue model in either two-dimensional sketching or three-dimensional modeling environments to correct, clarify, add, modify, remove or generally change the imported or originally produced geometry. The method can be done with bound or unbound constraints and can be driven by individual changes, a lookup table or a mathematical equation bound by user defined variables.

Figure 6:
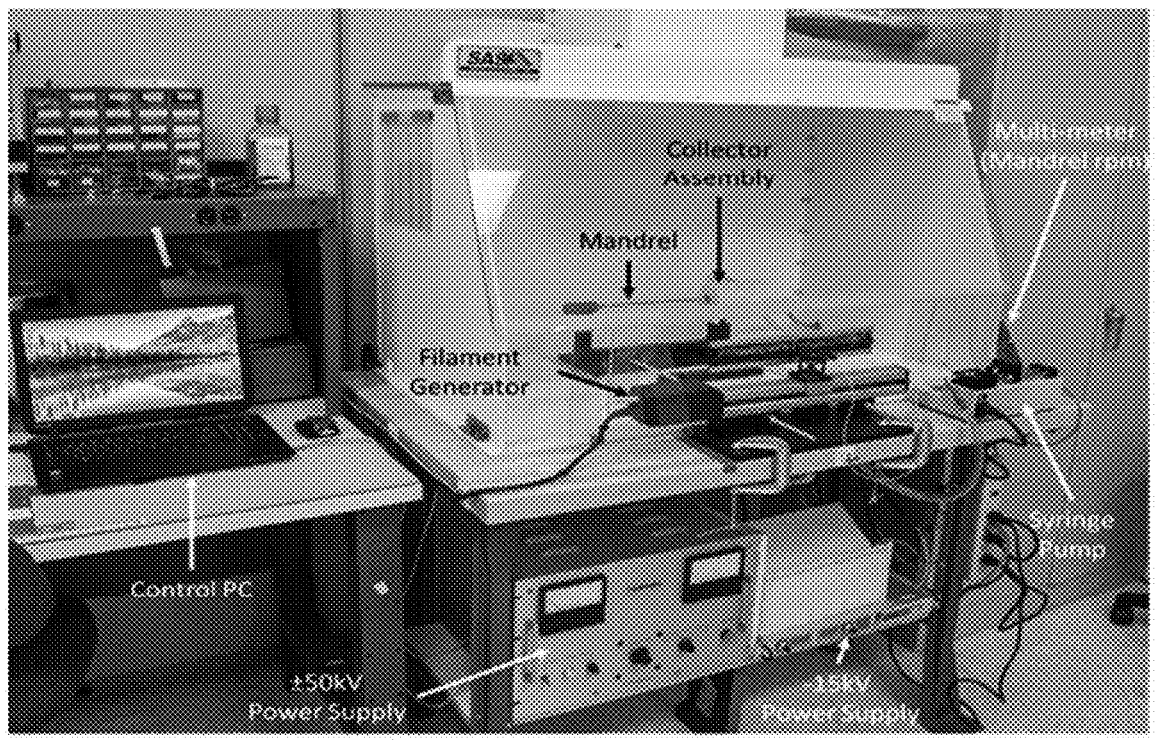
FIG. 6 is a perspective view of prior art terrestrial electrospinning hardware used to make prefabricated structures that can be incorporated into bioprinted tissues.
Figure 7:
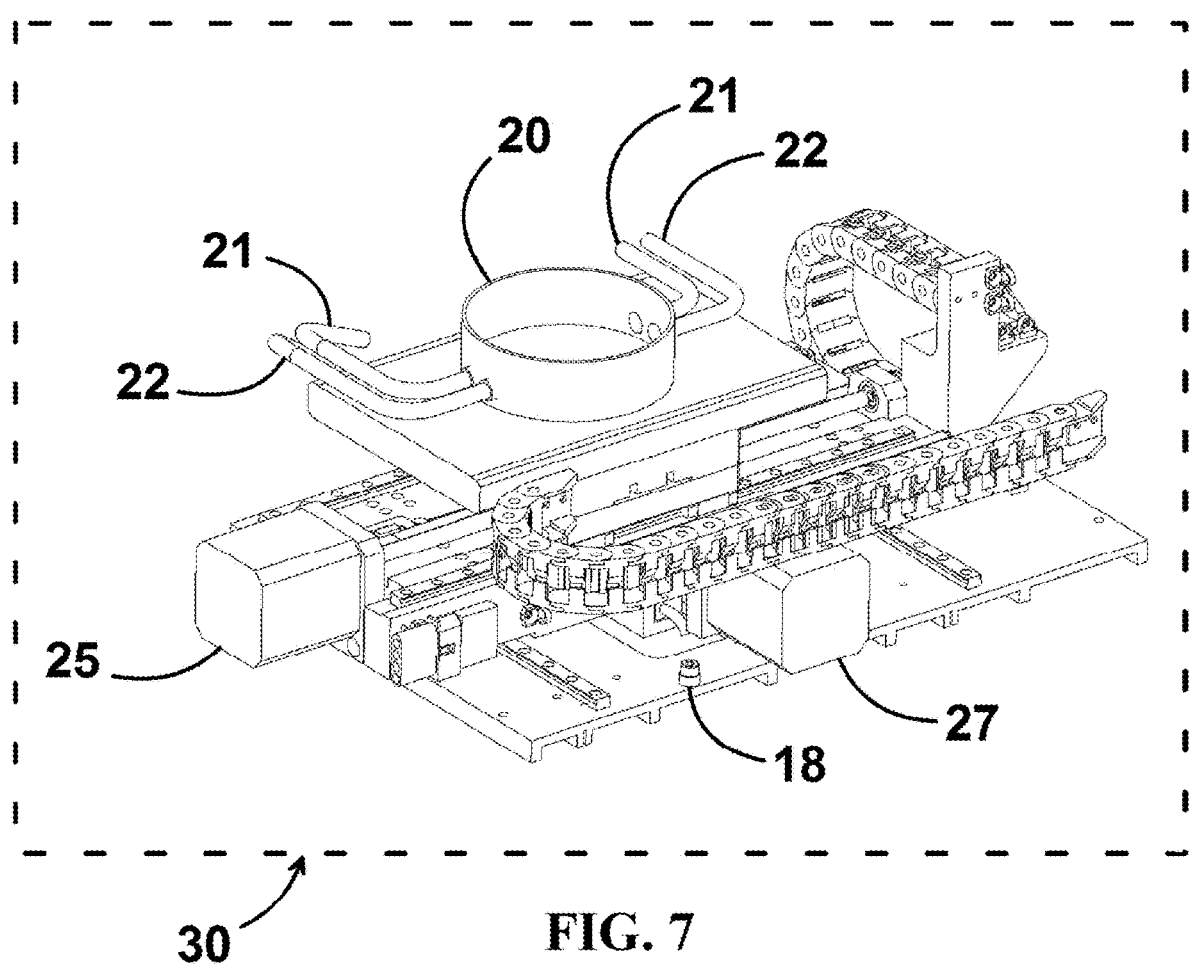
FIG. 7 is a perspective view of an embodiment of the print stage including a flexible bioreactor capable of mechanical and electrical stimulation of a printed tissue.

Some biomanufactured tissues or organs may include prefabricated structures such as large blood vessels that are incorporated before, during, or after 3D bioprinting in reduced gravity. Prefabricated structure of the tissue or organ can be created by at least one of electrospinning, electrospraying, electroaerosoling, or electrosputtering and can have three-dimensional scaffolds within or upon the bioprinted tissue or organ (See FIG. 6 prior art electrospinning hardware). This method can be used for at least one of the creation of the tissue or organ, support structure, perfusion aid, implantation aid, cell delivery, or reagent delivery. Additionally, prefabricated sensors can be incorporated into the 3D printed biomaterial or printed in place using electrically conductive biocompatible feed stock. These incorporated sensors may have the ability to provide data during the maturation process or following implantation in a target organism such as a human patient.

The reduced gravity biomanufacturing system may include a material dispensing system capable of printing bioinks. One method of manufacturing includes wherein part or all of the tissue may be created using a print head utilizing a direct-write printing approach driven by mechanical plunger driven by vacuum, pressurized gas, pressurized fluid, linear motor, or drive screw to express the bioink. The dispenser tips for the print head can have a single or multiple bores to express one or more bioinks simultaneously. The dispenser tips can be driven by a single or multiple print heads. The system can contain one single material or multiple materials. The method wherein part or all of the structure of the tissue or organ can be created by at least one of electrospinning, electrospraying, electroaerosoling, or electrosputtering. The methods can incorporate three-dimensional scaffolds within or upon the bioprinted tissue or organ. The methods can be used for at least 1 of the creation of the tissue or organ, support structure, perfusion aid, implantation aid, cell delivery, or reagent delivery. The reduced gravity biomanufacturing system may print an accurate, biologically viable reproduction of the desired tissue or organ and can transfer the printed tissue or organ into a perfused bioreactor chamber upon completion of printing automatically. Alternatively, the transfer may be done manually. The process can be performed robotically with reduced damage or contamination of the tissue or organ printed. The reduced gravity biomanufacturing system may culture the printed tissue or organ automatically to mature the tissue. The system may provide a method to perfuse the tissue and the developing vascular network. The system may allow the tissue to be removed from the reduced gravity biomanufacturing system and returned to Earth while remaining viable and suitable for transplant. The reduced gravity biomanufacturing system can be cleaned in place and reset with expendable bioreactor chamber, print head cartridges, dispenser tips, media, bioinks and image file by an astronaut and verified remotely.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It is to be understood that the embodiments are not limited in its application to the details of construction and the arrangement of components set forth in the description or illustrated in the drawings. The invention is capable of other embodiments and of being practiced or of being carried out in various ways. Unless limited otherwise, the terms "connected," "coupled," "in communication with," and "mounted," and variations thereof herein are used broadly and encompass direct and indirect connections, couplings, and mountings. In addition, the terms "connected" and "coupled" and variations thereof are not restricted to physical or mechanical connections or couplings.

The foregoing description of several embodiments of the invention has been presented for purposes of illustration. It is not intended to be exhaustive or to limit the invention to the precise steps and/or forms disclosed, and obviously many modifications and variations are possible in light of the above teaching.

What is claimed is:

1. A method for the additive manufacturing of living tissue in a reduced gravity environment comprising:
   providing a reduced gravity environment;
   providing a manufacturing facility for use in said reduced gravity environment, said manufacturing facility having a housing containing therein a bioprinter and a cell culturing bioreactor, wherein said cell culturing bioreactor defines an interior;
   providing one or more bioinks in fluid communication with said bioprinter, wherein said cell culturing bioreactor is in fluid communication with said one or more bioinks from said bioprinter, wherein said one or more bioinks comprises one or more cells;
   printing one or more three-dimensional tissues with said one or more bioinks from said bioprinter into said interior of said cell culturing bioreactor having no media therein within said reduced gravity environment;
   supplying said interior of said cell culturing bioreactor containing said one or more three-dimensional tissues with liquid media; and
   incubating said one or more three-dimensional tissues within said cell culturing bioreactor to promote at least one of cell proliferation, differentiation, and remodeling into a final product tissue.

2. The method of claim 1 wherein said cell culturing bioreactor is positioned on at least one print stage of said bioprinter.

3. The method of claim 2 wherein said cell culturing bioreactor is removable from said at least one print stage of said bioprinter.

4. The method of claim 1 wherein said one or more bioinks further include non-living biological components, wherein said non-living biological components include at least one of natural or synthetic structural proteins, polymers, macromolecules, or pharmaceuticals.

5. The method of claim 1 wherein said reduced gravity environment is an environment wherein the gravitational acceleration is less than 9.807 meters per second per second.

6. The method of claim 1 wherein said one or more bioinks further include biological components, wherein said biological components include at least one of microvascular fragments or organelles.

7. The method of claim 1 wherein said one or more cells in said one or more bioinks include at least one of undifferentiated stem cells, partially differentiated stem cells, or terminally differentiated cells.

8. The method of claim 1 further comprising the step of maturing said one or more three-dimensional tissues within said cell culturing bioreactor in said reduced gravity environment.

9. The method of claim 1 wherein said one or more bioinks have a viscosity range of about 1 to 10,000,000 centipoise.

10. The method of claim 9 wherein said viscosity range is about 5 to 2,000 centipoise.

11. The method of claim 1 further comprising the step of controlling at least one of temperature or humidity within said housing.

12. The method of claim 1 further comprising the steps of providing one or more print stages, and controlling the thermal characteristics of said one or more print stages.

13. The method of claim 1 further comprising the steps of providing one or more print heads, and controlling the thermal characteristics of said one or more print heads.

14. The method of claim 1 further comprising the step of controlling the temperature of said one or more bioinks.

15. The method of claim 1 further comprising the step of at least partially controlling the additive manufacturing of living tissue in the reduced gravity environment from one or more locations, wherein at least one location is terrestrial.

16. The method of claim 1 further comprising the step of transporting said one or more three-dimensional tissues from said reduced gravity environment to a different gravity environment.

17. The method of claim 16 wherein said different gravity environment is at least one of a terrestrial environment or an extraterrestrial environment.

18. The method of claim 1 further comprising the step of incorporating prefabricated structure into said one or more three dimensional tissues for at least one of the creation of the tissue or organ, support structure, perfusion aid, implantation aid, cell delivery, or reagent delivery.

19. The method of claim 1 further comprising the steps of removing said cell culturing bioreactor out of fluid communication with said bioprinter, and subsequently providing a second cell culturing bioreactor within said housing in fluid communication with said bioprinter.

20. A method for the additive manufacturing of living tissue in a reduced gravity environment comprising:
   providing a reduced gravity environment;
   providing a manufacturing facility for use in said reduced gravity environment, said manufacturing facility including a housing, said housing having a bioprinter positioned therein;
   providing one or more bioinks in fluid communication with said bioprinter, wherein said one or more bioinks comprises one or more cells;
   providing a plurality of cell culturing bioreactors for removable fluidic communication with said bioprinter;
   positioning a first cell culturing bioreactor of said plurality of cell culturing bioreactors within said housing in fluid communication with said one or more bioinks from said bioprinter;
   printing one or more three-dimensional tissues with said one or more bioinks without a crosslinking agent from said bioprinter into an interior of said first cell culturing bioreactor within said reduced gravity environment;
   removing said first cell culturing bioreactor of said plurality of cell culturing bioreactors from fluid communication with said bioprinter;
   supplying said interior of said first cell culturing bioreactor containing said one or more three-dimensional tissues with liquid media; and
   incubating said one or more three-dimensional tissues within said first cell culturing bioreactor to promote at least one of cell proliferation, differentiation, and remodeling into a final product tissue.

21. A method for the additive manufacturing of living tissue in a reduced gravity environment comprising:
   providing a reduced gravity environment;
   providing a manufacturing facility for use in said reduced gravity environment, said manufacturing facility including a housing, said housing having a bioprinter positioned therein;
   providing one or more bioinks in fluid communication with said bioprinter; and
   providing a plurality of cell culturing bioreactors for removable fluidic communication with said bioprinter;
   positioning a first cell culturing bioreactor of said plurality of cell culturing bioreactors within said housing in fluid communication with said one or more bioinks from said bioprinter;
   printing one or more three-dimensional tissues with said one or more bioinks from said bioprinter into an unoccupied interior of said first cell culturing bioreactor within said reduced gravity environment;
   removing said first cell culturing bioreactor of said plurality of cell culturing bioreactors from fluid communication with said bioprinter;
   positioning a second cell culturing bioreactor of said plurality of cell culturing bioreactors within said housing in fluid communication with said one or more bioinks from said bioprinter; and
   printing one or more three-dimensional tissues with said one or more bioinks from said bioprinter into an interior of said second cell culturing bioreactor within said reduced gravity environment.

22. The method of claim 21 further comprising the step of incubating the one or more three-dimensional tissues in liquid media after printing.

* * * * *